(12) United States Patent
Shamoo et al.

(10) Patent No.: US 8,748,147 B2
(45) Date of Patent: Jun. 10, 2014

(54) HIGH PROCESSIVITY POLYMERASES

(75) Inventors: Yousif Shamoo, Houston, TX (US); Siyang Sun, Lafayette, IN (US)

(73) Assignee: William Marsh Rice University, Houston, TX (US)

( * ) Notice: Subject to any disclaimer, the term of this patent is extended or adjusted under 35 U.S.C. 154(b) by 1511 days.

(21) Appl. No.: 11/945,877

(22) Filed: Nov. 27, 2007

(65) Prior Publication Data

US 2011/0217737 A1    Sep. 8, 2011

Related U.S. Application Data

(63) Continuation of application No. PCT/US2006/020801, filed on May 30, 2006.

(60) Provisional application No. 60/685,187, filed on May 27, 2005.

(51) Int. Cl.
*C12N 9/12* (2006.01)
*C12P 21/04* (2006.01)

(52) U.S. Cl.
USPC ........... 435/194; 435/183; 435/69.7; 530/350

(58) Field of Classification Search
None
See application file for complete search history.

(56) References Cited

U.S. PATENT DOCUMENTS

| 7,541,170 B2 * | 6/2009 | Wang et al. ............... 435/194 |
| 7,666,591 B2 * | 2/2010 | Kowalczykowski et al. .. 435/6.1 |
| 2002/0119467 A1 | 8/2002 | Pelletier et al. |
| 2004/0002076 A1 | 1/2004 | Wang et al. |

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
Borjac-Natour et al. (Virology Journal, vol. 1:4, doi:10.1186/1743-422X-1-4, Sep. 17, 2004.*
Sun et al., Proteins, vol. 65, No. 1, pp. 231-238, Oct. 2006.*
Wang, et al., J. Biol. Chem., 270:26558-64 (1995), Nov. 1995.
Enterobacteria phage RB69 complete genome, 2003.
Wang, C.C., Modular Organization of T4 DNA Polymerase, Journal of Biological Chemistry, Nov. 1995, vol. 270, No. 44, pp. 26558-26564, entire document, especially p. 26558.
Enterobacteria phage RB69 complete genome, Genome Sequence [online], 2003 [retrieved on May 15, 2007], retrieved from the Internet: <RUL: http://www.ncbi.nlm.nih.gov/entrez/viewer.fcgi?val=NP_861936.1>.
International Search Report for PCT/US2006/20801 dated Aug. 22, 2007.

* cited by examiner

*Primary Examiner* — Richard Hutson
(74) *Attorney, Agent, or Firm* — Reed Smith LLP; Robert R. Riddle

(57) ABSTRACT

Chimeric proteins comprising a sequence nonspecific single-stranded nucleic-acid-binding domain joined to a catalytic nucleic-acid-modifying domain are provided. Methods comprising contacting a nucleic acid molecule with a chimeric protein, as well as systems comprising a nucleic acid molecule, a chimeric protein, and an aqueous solution are also provided. The joining of sequence nonspecific single-stranded nucleic-acid-binding domain and a catalytic nucleic-acid-modifying domain in chimeric proteins, among other things, may prevent the separation of the two domains due to their weak association and thereby enhances processivity while maintaining fidelity.

8 Claims, 10 Drawing Sheets
(6 of 10 Drawing Sheet(s) Filed in Color)

Figure 6
a.
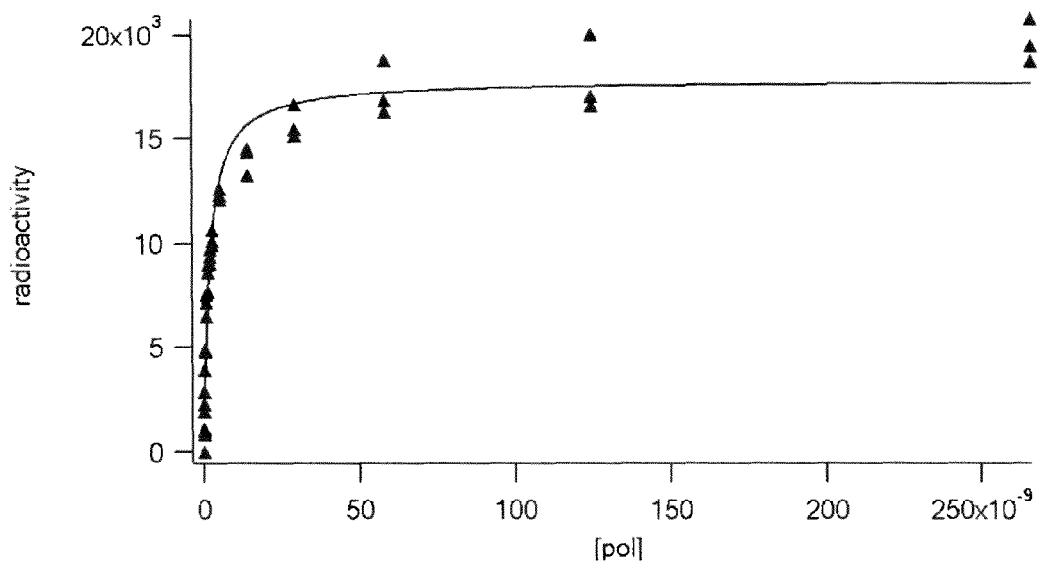
b.
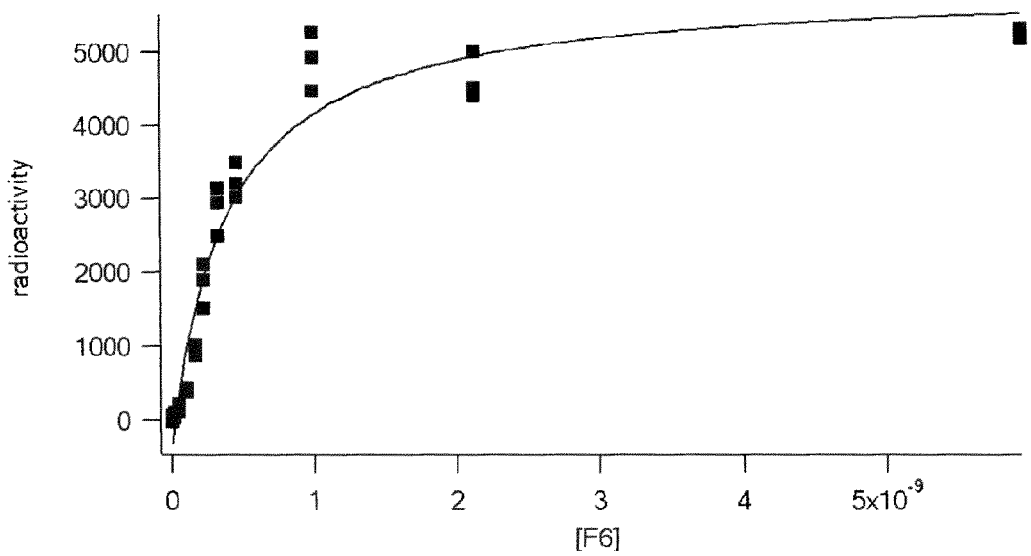

HIGH PROCESSIVITY POLYMERASES

CROSS-REFERENCE TO RELATED APPLICATIONS

This application is a continuation of International Application No. PCT/US2006/020801, filed May 30, 2006, which claims the benefit of U.S. Provisional Application No. 60/685,187, filed May 27, 2005.

This disclosure includes a sequence listing submitted as a text file pursuant to 37 C.F.R. §1.52(e)(v) named replacement sequence listing.txt, created on Mar. 19, 2008, with a size of 1,152 bytes, which is incorporated herein by reference. The attached sequence descriptions and Sequence Listing comply with the rules governing nucleotide and/or amino acid sequence disclosures in patent applications as set forth in 37 C.F.R. §§1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (No. 2):345-373 (1984). The symbols and format used for nucleotide and amino acid sequence data comply with the rules set forth in 37 C.F.R. §1.822.

STATEMENT OF GOVERNMENT INTEREST

This disclosure was made with support under Grant Number RSG-03-051-01-GMC awarded by the American Cancer Society and Contract No. W-31-109-ENG-38 awarded by the U.S. Department of Energy, Office of Energy Research. The U.S. government has certain rights in the invention.

BACKGROUND

The complex processes of DNA replication, recombination, and repair all require that the DNA double-helix be at least transiently unwound. In DNA replication, helicases bind to parental DNA and unwind it so that DNA polymerase may read the genetic code to synthesise a new copy or daughter strand. As the duplex DNA is unwound, a class of proteins called SSBs (derived from single-stranded DNA binding proteins) are responsible for binding single-stranded DNA (ssDNA) until it is utilised by DNA polymerase or other proteins involved in DNA recombination and repair.

DNA polymerases generally are divided according to the correspondence in their amino acid sequences into three main families with subclasses. In prokaryotes, the main distinction is made between three polymerases: polymerase I, II, and III. These polymerases differ with regard to their function in the cell and with regard to their properties. DNA polymerase I is considered to be a repair enzyme and frequently has 5'-3' as well as 3'-5' exonuclease activity. Polymerase II appears to facilitate DNA synthesis which starts from a damaged template strand and thus preserves mutations. Polymerase III is the replication enzyme of the cell, it synthesizes nucleotides at a high rate (ca. 30,000 per minute) and is considered to be very processive. Polymerase III has no 5'-3' exonuclease activity.

Particular properties of polymerases are desirable depending on the application. For example, in PCR, thermophilic DNA polymerases are used to perform cyclical primer-extensions at high temperature to amplify the number of copies of a DNA product. The length, quality, and quantity of this product depend on the accuracy, stability, and processivity of the DNA polymerase.

In vivo, replicative DNA polymerases are made more processive by their interactions with accessory proteins, like SSBs, at the replication fork. SSBs are essential proteins that bind tightly and cooperatively to ssDNA during replication to remove adventitious secondary structures and protect the exposed DNA from endogenous nucleases. Historically, SSBs have sometimes been loosely referred to as "helix-destabilising proteins" because they can reduce the stability or "melt" some duplex DNAs. It should be emphasised that SSBs do not unwind dsDNA, rather, they bind and stabilise the ssDNA conformation as it becomes available either enzymatically via helicases or by binding ssDNA "bubbles" or the transiently frayed 5' or 3' ends of an otherwise duplex DNA. Because SSBs must bind all available ssDNA as it becomes accessible, they are highly abundant.

FIGURES

A more complete understanding of this disclosure may be acquired by referring to the following description taken in combination with the accompanying figures.

The patent or application file contains at least one drawing executed in color. Copies of this patent or patent application publication with color drawing(s) will be provided by the Office upon request and payment of the necessary fee.

FIG. 1 is a schematic diagram depicting replication of a nucleic acid with the help of accessory proteins.

FIG. 2 (A) is an image of a polyacrylamide gel electrophoresis of PCR reaction products using 5' end $^{32}$P labeled 20-mer primers, according to specific example embodiments of the present disclosure. (B) is an image of a polyacrylamide gel electrophoresis of PCR reaction products using 5' end $^{32}$P labeled 20-mer primers, according to specific example embodiments of the present disclosure.

FIG. 6 is a graph of the results from a filter binding assay for (a) RB69 DNA polymerase and (b) F6 according to specific example embodiments of the present disclosure.

Figure 8:
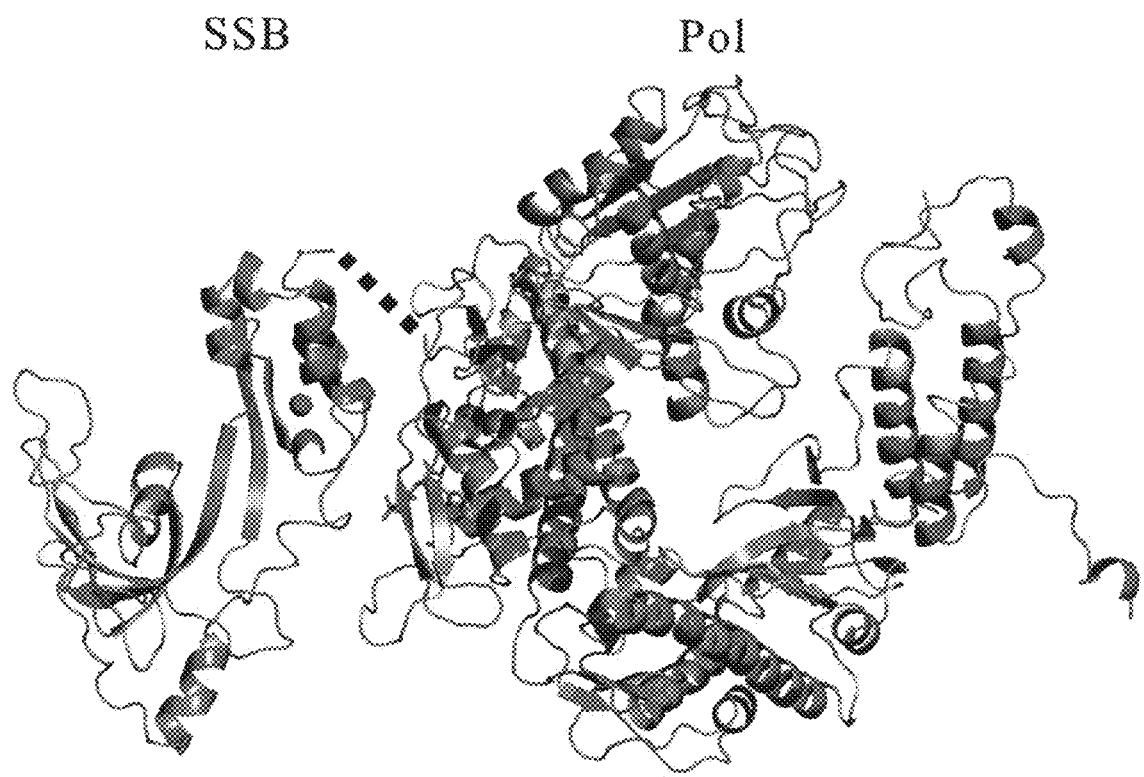

FIG. 8 is a chimeric protein structure composite ribbon diagram showing the structure of F6 with a Zinc atom bound by SSB and a GDP bound by DNA polymerase generated using PYMOL, according to specific example embodiments of the present disclosure. Color coding is based on crystallographic temperature factors (B), with red representing regions of higher B factors and blue representing regions of lower B factors (B factor range 1-100). The linker and 12 amino acids from the C-terminus of RB69 SSB core domain are highly flexible and were not seen in the electron density region connecting the C-terminus of SSB to N-terminus of DNA polymerase.

Figure 9:
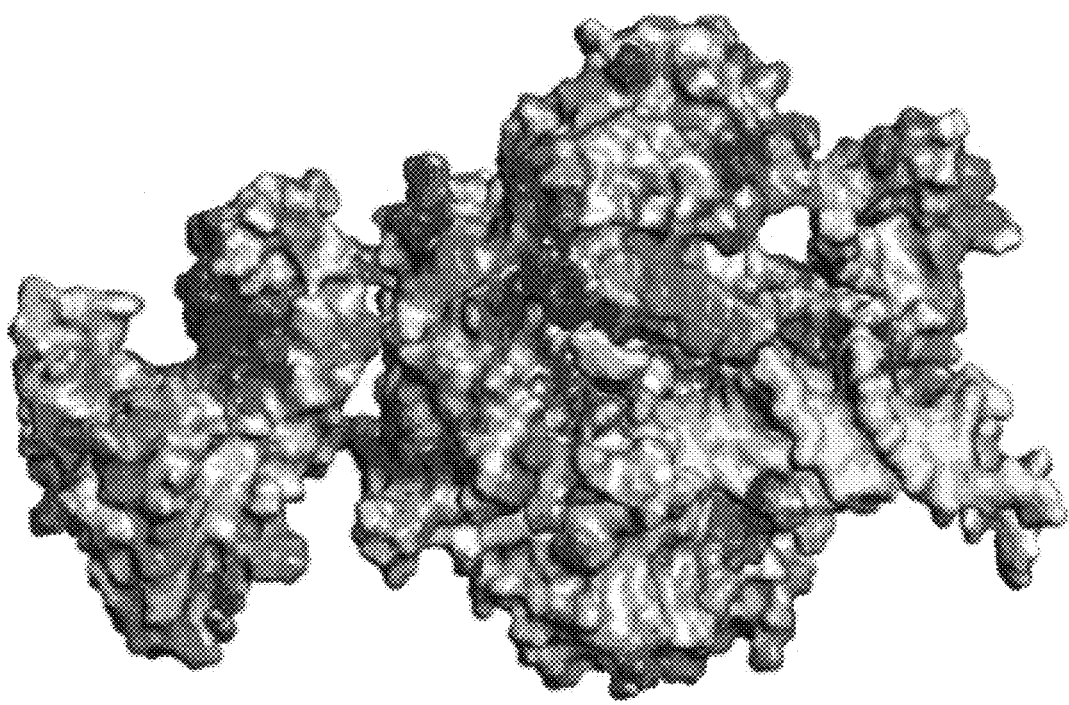

FIG. 9 is a chimeric protein structure composite showing surface charge distribution of F6, according to specific example embodiments of the present disclosure.

Figure 10:
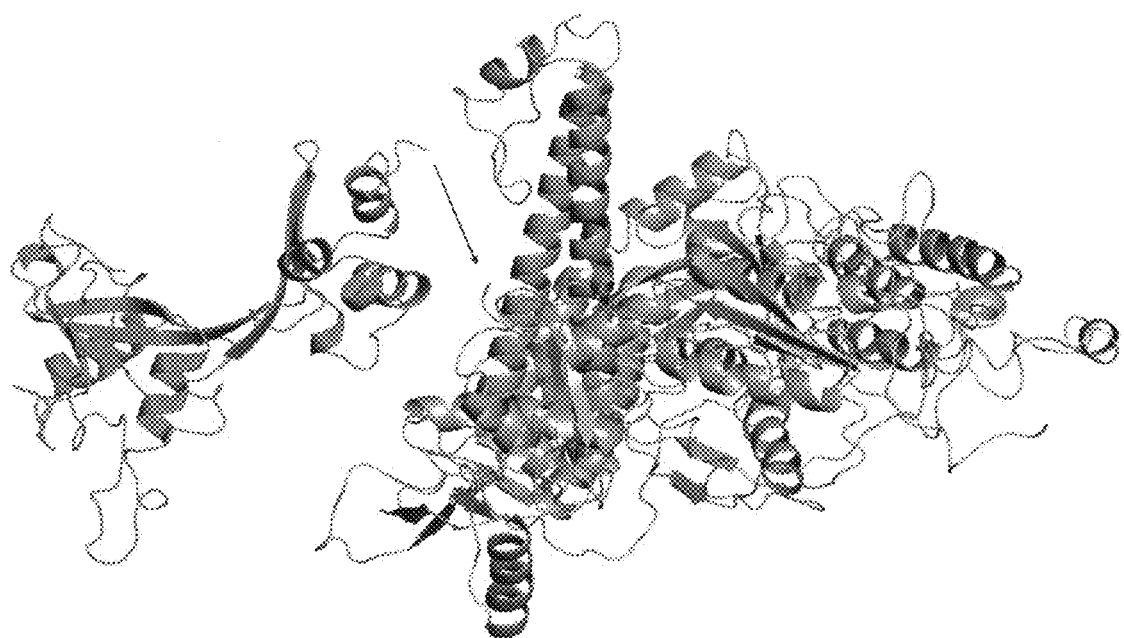

FIG. 10 shows a ribbon diagram of an F6 formed from the joining of an RB69 SSB core and DNA polymerase, according to specific example embodiments of the present disclosure.

The patent or application file contains at least one drawing executed in color. Copies of this patent or patent application publication with color drawing(s) will be provided by the Patent Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

SUMMARY

The present disclosure, according to one embodiment, relates to a chimeric protein comprising at least two heterologous domains: a sequence nonspecific single-stranded nucleic-acid-binding domain joined to a catalytic nucleic-acid-modifying domain. In other embodiments, the present disclosure also provides methods that use a chimeric protein, as well as systems that include a chimeric protein.

In the absence of DNA substrate, the interaction between DNA polymerase and SSB is weak and transient. The joining of sequence nonspecific single-stranded nucleic-acid-binding domain and a catalytic nucleic-acid-modifying domain in chimeric proteins, among other things, may prevent the separation of the two domains due to their weak association and thereby enhances processivity while maintaining fidelity.

Further, the chimeric proteins of the present disclosure have demonstrated an enhanced ability to move through DNA secondary structures. The SSB family of proteins can destabilize secondary structures by binding preferentially to ssDNA to shift the equilibrium away from the adventitious structures. In the case of the chimeric proteins of the present disclosure, the higher affinity for the primer-template nucleic acid sequences suggests that the chimeric protein is less likely to dissociate and may have more opportunity to move through transient secondary structures as they breathe and the single stranded nucleic acid domain of the chimeric protein can bind the available single stranded nucleic acid sequences.

The features and advantages of the present invention will be readily apparent to those skilled in the art upon a reading of the description of the embodiments that follows.

DESCRIPTION

The present disclosure, according to one embodiment, relates to a chimeric protein comprising a catalytic nucleic-acid-modifying domain and a sequence nonspecific single-stranded nucleic-acid-binding domain. Such chimeric proteins may interact with a nucleic acid molecule that is a least partially single-stranded.

In certain embodiments, the present disclosure provides a chimeric protein comprising at least two joined heterologous domains in which the first domain is a sequence nonspecific single-stranded nucleic-acid-binding domain, and the second domain is a catalytic nucleic-acid-modifying domain. As used herein, the term "join" or "joined" refers to any means of operably connecting two proteins, for example, by means of a tether (e.g., an amino acid sequence). By way of explanation, and not of limitation, the presence of the sequence nonspecific single-stranded nucleic-acid-binding domain enhances the catalytic nature of the nucleic-acid-modifying domain compared to an identical protein not having a sequence-non-specific nucleic-acid-binding domain joined thereto.

The sequence nonspecific single-stranded nucleic-acid-binding domain may be any domain capable of binding a single-stranded nucleic acid molecule. One example of a suitable nonspecific single-stranded nucleic-acid-binding domain comprises amino acid residues 22-254 of gp32 from the T4-like bacteriophage RB69. Additional nucleic-acid-binding domains suitable for use in conjunction with the present disclosure can be identified by one or more of homology with known sequence nonspecific single-stranded DNA binding proteins, antibody crossreactivity, or biochemical assay.

The catalytic nucleic-acid-modifying domain may comprise a thermophilic polymerase domain. For example, the thermophilic polymerase domain may be a DNA polymerase domain present in a thermophilic DNA polymerase, such as one from the DNA polymerase in *Thermus aquaticus, Thermus thermophilus*, Vent DNA polymerase, or *Bacillus sterothermophilus* DNA polymerase. Alternatively, the catalytic domain may be an RNA polymerase, an exonuclease, or other nucleic-acid-modifying enzyme that has single-stranded DNA or RNA as its principle substrate. One specific example of a suitable catalytic nucleic-acid-modifying domain is the N-terminus of RB69 DNA polymerase.

The catalytic nucleic-acid-modifying domain and the single-stranded nucleic-acid-binding domain may be joined by methods well known to those of skill in the art. These methods include chemical and recombinant means. Chemical means of joining the heterologous domains are described, for example, in Bioconjugate Techniques, Hermanson, Ed., Academic Press (1996). Such techniques include, for example, peptidyl bond formation and derivitization for the purpose of linking the moieties to each other, either directly or through a linking compound, by methods that are well known in the art of protein chemistry.

The catalytic nucleic-acid-modifying domain and the single-stranded nucleic-acid-binding domain may be joined by a tether, such as an amino acid sequence (e.g., a peptide). Such tethers may be formed using chemical methods to synthesize an amino acid sequence in whole, or in part. For example, peptides can be synthesized by solid phase techniques, such as, for example, the Merrifield solid phase synthesis method, in which amino acids are sequentially added to a growing chain of amino acids. Equipment for automated synthesis of peptides is commercially available from suppliers such as PE Corp. (Foster City, Calif.), and may generally be operated according to the manufacturer's instructions. The synthesized peptides can then be cleaved from the resin, and purified, for example, by preparative high performance liquid chromatography. One example of an amino acid sequence suitable for use as a tether comprises Gly-Thr-Gly-Ser-Gly-Thr (SEQ ID NO. 1).

Accordingly, in certain embodiments, a chimeric protein may comprise a nucleic-acid-modifying domain (e.g., a nucleic acid polymerase), a sequence non-specific single-stranded nucleic acid binding domain (e.g., a SSB from the bacteriophage RB69, such as the amino acid residues 22-254 of gp32), and an amino acid tether (e.g., Gly-Thr-Gly-Ser-Gly-Thr) (SEQ ID NO. 1), in which the tether is bound to the nucleic-acid-modifying domain and the sequence non-specific single-stranded nucleic acid binding domain.

In addition to the catalytic nucleic-acid-modifying domain and sequence nonspecific single-stranded nucleic-acid-binding domain, in some embodiments the chimeric protein may further comprise another domain. For example, the chimeric protein may comprise a thioredoxin, among other things, to further increase the processivity of the protein. In another example, the chimeric protein may comprise a sequence nonspecific double-stranded nucleic-acid-binding domain such as, for example, a sliding clamp protein, or portion thereof.

The chimeric proteins of the present disclosure are generally more processive than their native forms. Accordingly, these chimeric proteins may be useful in a variety of applications, for example, polymerase chain reaction (PCR), DNA sequencing, or other reactions using enzymatic sequencing of DNA. By way of explanation, and not of limitation, the tighter binding of such chimeric proteins to the primer-template junction, together with the ability of the sequence non-specific single-stranded nucleic acid binding domain to destabilize secondary structures on the template strand, may be responsible for higher processivity.

The present disclosure, according to another embodiment, relates to methods that comprise contacting a nucleic acid molecule with a chimeric protein having at least two heterologous domains, wherein a first domain that is a sequence non-specific single-stranded nucleic-acid-binding domain is joined to a second domain that is a catalytic nucleic-acid-modifying domain, where the presence of the sequence-non-specific single-stranded nucleic-acid-binding domain stabilizes the formation of a single-stranded nucleic acid compared to an otherwise identical protein not having the sequence-non-specific single-stranded nucleic-acid-binding domain joined to it.

According to another embodiment, the present disclosure provides a system comprising a nucleic acid molecule, a chimeric protein having at least two heterologous domains, wherein a first domain that is a sequence non-specific single-stranded nucleic-acid-binding domain is joined to a second domain that is a catalytic nucleic-acid-modifying domain by a tether, and an aqueous solution that permits the binding domain to bind to the nucleic acid molecule and that permits the chimeric protein to function in a catalytic manner to modify the nucleic acid molecule.

To facilitate a better understanding of the present disclosure, the following examples of specific embodiments are given. In no way should the following examples be read to limit or define the entire scope of the invention.

EXAMPLES

As a specific example embodiment, the C-terminus of RB69 SSB core domain was connected to the N-terminus of RB69 DNA polymerase by a flexible six amino acid linker to form a chimeric protein of the present disclosure (i.e. F6) and a noticeable increase in processivity was observed. DNA replication in RB69 (a T4-like bacteriophage) is similar to those of eukaryotes and archae, and has been a prototype for studies on DNA replication and assembly of the functional replisome. Limited proteolysis has shown that the RB69 gp32 can be divided into three distinct domains. The N-terminal "B-domain" (residues 1-21) is essential for the cooperative binding of RB69 SSB to ssDNA. The C-terminal "A-domain" (residues 255-299) is highly acidic and mediates interactions with other proteins involved in DNA replication, recombination, and repair. The core domain (residues 22-254) is the DNA-binding domain and has the same intrinsic affinity as the intact protein for short single-stranded DNA.

The interaction between RB69 DNA polymerase and single-stranded DNA binding protein shows a 60-fold increase in the overall affinity of RB69 SSB for template-strand DNA in the presence of DNA polymerase, which may arise from specific protein-protein interactions. But the C-terminal domain of RB69 single-stranded DNA-binding protein, previously suggested to be the site of RB69 DNA polymerase-SSB interactions, is dispensable.

Cloning and Overexpression of F6 gp32 core domain (residues 22-253) and gp43 were amplified by PCR and ligated into pET101-TOPO vector (Invitrogen). The primers were designed such that after ligation, the C-terminus of gp32 core domain (residues 21-253) was connected to the N-terminus of gp43 through a flexible linker (Gly-Thr-Gly-Ser-Gly-Thr) (SEQ ID NO. 1) from the single-stranded DNA binding protein C-terminus to the DNA polymerase N-terminus.

Expression and Purification of RB69 gp43 exo-, gp32 Proteins and F6

Clones for the overexpression of intact RB69 gp32 and gp32 core were generated previously as described in Sun S, Shamoo Y. Biochemical characterization of interactions between DNA polymerase and single-stranded DNA-binding protein in bacteriophage RB69. J Biol Chem 2003; 278(6): 3876-3881. RB69 DNA polymerase exo-, intact RB69 gp32, gp32 core domain were purified as described earlier. F6 protein was induced by 1 mM IPTG overnight and purified as follows. Cells were lysed and cell debris was removed by centrifugation. The supernatant was loaded onto a 60 ml P11 column, washed with buffer containing 10 mM HEPES pH 7.5, 250 mM NaCl and eluted with 10 mM HEPES pH 7.5, 500 mM NaCl. Fractions containing F6 were then dialyzed to 150 mM NaCl overnight and purified further using ion exchange chromatography (MonoQ). F6 protein was eluted with a linear salt gradient of 150 mM NaCl to 1M NaCl with 10 mM Tris-Cl pH 7.5. F6 protein was concentrated to 20 mg/ml, flash frozen in liquid nitrogen and stored in 10 mM HEPES pH 7.5, 150 mM NaCl, 1 mM EDTA, 0.3 mM DTT, and 5% (v/v) glycerol. Average yield for F6 protein is about 2 mg/l growth. SeMet F6 protein was generated by methionine pathway inhibition and was purified in a similar manner as the native F6 protein.

F6 Displayed Higher Processivity than RB69 DNA Polymerase

In order to insure that chimeric protein of the RB69 SSB core domain joined to RB69 DNA polymerase did not inhibit processivity, we compared the activity of RB69 DNA polymerase and F6 on M13 mp18 DNA primed with two different 20-mers (P1 and P2). DNA synthesis using M13mp18 as template DNA is frequently paused or arrested at sites throughout the sequence. When DNA polymerase dissociates from the primer-template junction, it can re-associate and resume DNA replication. In order to compare the processivity of F6 to RB69 DNA polymerase, a heparin trap was used to capture single-turnover events.

Figure 1:
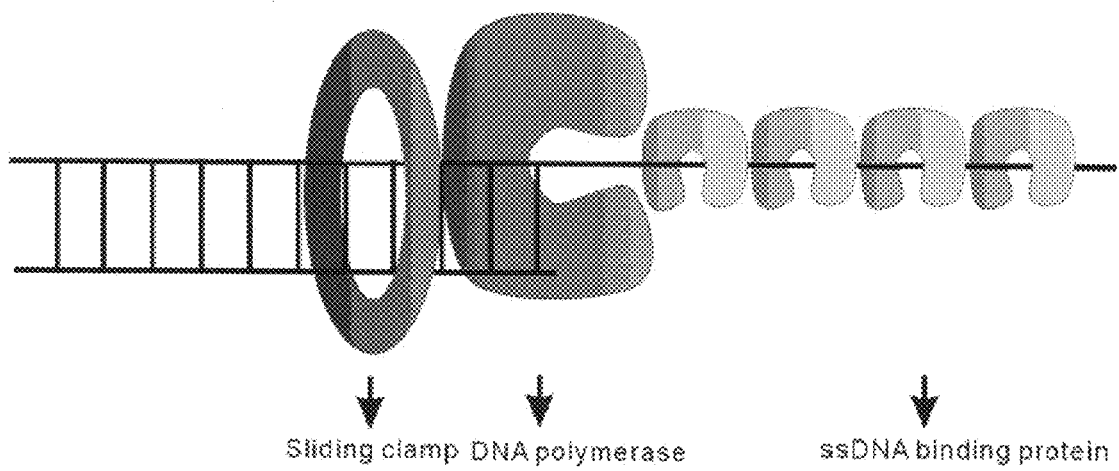
Figure 2:
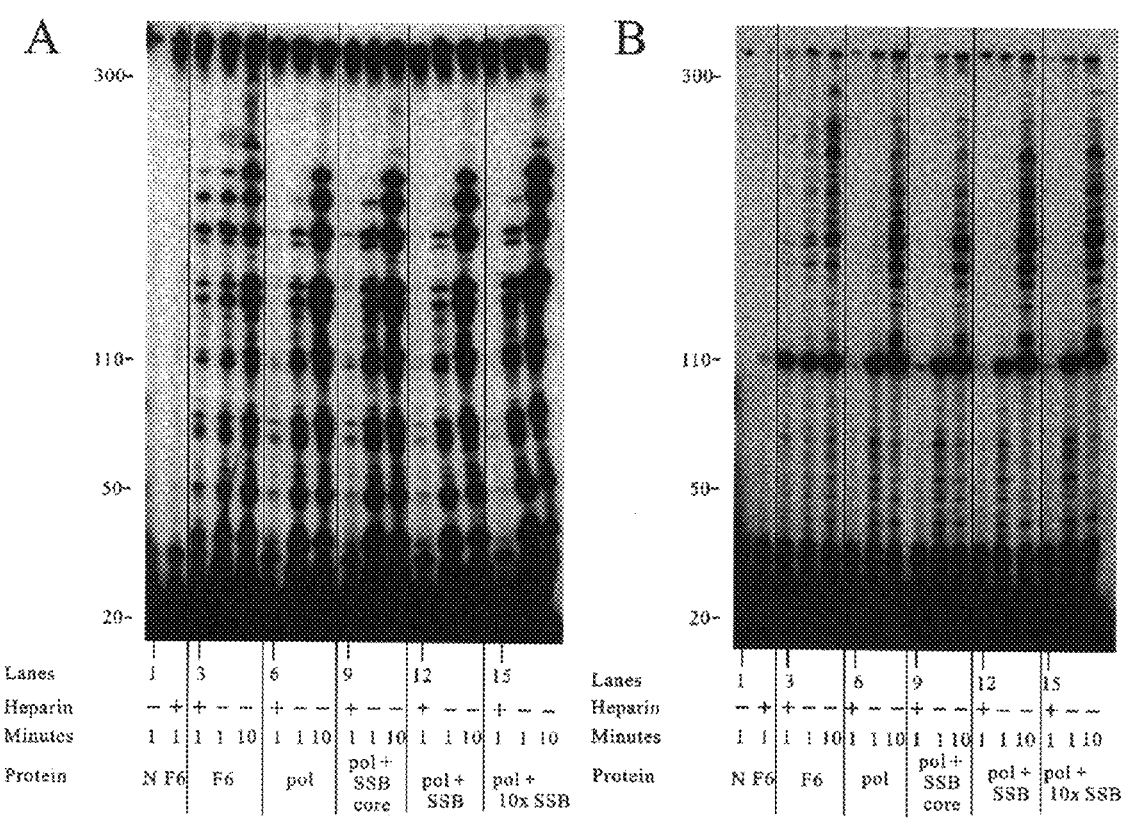

Polymerase processivity assays were carried out using two different sets of primers: P1 (5'-CCAGTCACGACGTTG-TAAAA-3') (SEQ ID NO. 2) or P2 (5'-GCGGGGAGAG-GCGGTTTGCG-3') (SEQ ID NO. 3) annealed to M13 mp18. Primers were 5' end labeled with $^{32}$P and purified on a NICK column (Pharmacia). Each reaction mixture (4 μl total volume) contained 1.8 nM annealed primer-template, 250 μM dNTPs, 25 mM Tris-Cl pH7.5, 60 mM KCl, 10 mM DTT, 200 μg/ml BSA, and 1 mM EDTA. Reaction mixtures were incubated with 1.8 nM protein or combinations of proteins at 30° C. for 2 mins and the reactions initiated by the addition of $MgCl_2$ to a final concentration of 6 mM. Single turnover reaction conditions were achieved by the addition of heparin to a final concentration of 500 μg/ml together with MgCl₂ in the initiation buffer. The presence of a high concentration of heparin ensured that once DNA polymerase dissociates, it binds to heparin instead of re-associating with the primer-template junction. Reactions were stopped at different time points by addition of 6 μl loading buffer containing 83% (v/v) formamide, 0.01% (w/v) xylene cyanol, 0.01% (w/v) bromphenol blue and 33 mM EDTA. Products were boiled for 5 mins and fractionated on 6% polyacrylamide-7M urea gels as shown in FIG. 2. A. Lane 1: Reaction mixture without enzyme. Lane 2: Heparin was added before F6 as a control to show that the chimeric protein binds heparin and that it is therefore an effective single-turnover sink. Lane 3-15: Reactions with different protein and protein combinations with/without heparin at different time points. The intensity of the products was analyzed by phosphorimaging as described in Spacciapoli P, Nossal NG. A single mutation in bacteriophage T4 DNA polymerase (A737V, tsL141) decreases its processivity as a polymerase and increases its processivity as a 3'→5' exonuclease. *J Biol Chem* 1994; 269(1):438-446. Processivity was calculated as described in Von Hippel, et al. *Ann NY Acad Sci* 1994; 726:118-131. The product intensities were plotted as $\log(n_I/n_T)$ versus $n-1$, where n is the number of nucleotides incorporated at position I, $n_I$ is the intensity of extended primers that terminate at position I and $n_T$ is the sum of the intensities of extended primers that terminate at and before position I. The data was fitted with IgorPro (Wavemetrics, CA) to the following equation: $\log(n_I/n_T)=(n-1)\log P_I + \log(1-P_I)$, where $P_I$ is defined as the "microscopic processivity parameter" for position I, the probability of not terminating at position I. The average primer extension length was determined from $1/(1-P_I)$.

Figure 3:
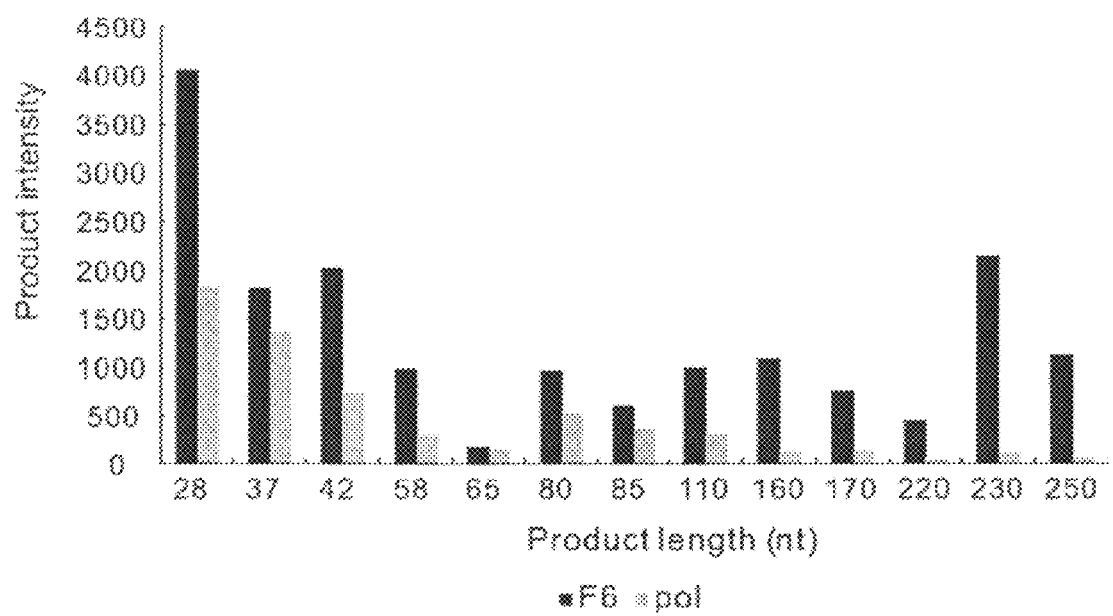
FIG. 3 shows product intensity from F6 and RB69 DNA polymerase processivity assays measured using P1/M13 mp18 as primer-template DNA and analyzed by phosphorimaging, according to specific example embodiments of the present disclosure.

F6 displayed a much higher processivity than RB69 DNA polymerase (compare lanes 3 and 6 in FIG. 2). F6 can overcome more arrest sites than RB69 DNA polymerase and yielded products of much longer size (FIG. 3). The synthesis of larger DNA products is the result of higher processivity as shown by comparing the results of single versus multi-turnover reactions. The amount and length of products produced under multi-turnover conditions are comparable (lanes 5, 8 in FIG. 2) whereas single turnover conditions produce striking changes in both length and quantity (lanes 4, 7 in FIG. 2). Mixtures of RB69 DNA polymerase and different SSB constructs were also tested and showed that F6 is more processive under single turnover conditions. Reactions with heparin were also conducted for longer times and as expected, showed no significant differences from 1 min reaction times (data not shown). There was a seven-fold increase in processivity for F6 compared to RB69 DNA polymerase as determined by the increase of average primer extension length as shown in Table 1.

TABLE 1

| Enzyme | Microscopic processivity ($P_I$) | Average primer extension length (nt) [$1/(1-P_I)$] |
|---|---|---|
| F6 | 0.997 ± 0.001 | 314.4 |
| RB69 DNA polymerase | 0.978 ± 0.003 | 45.5 |

The ability of F6 to overcome arrest sites are shown in the reactions using P1 as primer. P1 anneals to a region on M13 mp18 105 nt downstream from a major replication pause site (12 bp hairpin structure). As shown in lane 3, F6 is more efficient in overcoming this major pause site and continue DNA synthesis, while DNA polymerase and mixtures of DNA polymerase and SSB and core SSB do not (lanes 6, 9, 12, 15 in FIG. 2). Similarly, without heparin present, F6 still displayed higher processivity than RB69 DNA polymerase for short reaction times, but the effect was much less distinguishable for longer reaction times due to the reinitiation of DNA synthesis through multiple binding events.

In Vitro Fidelity Assay Shows F6 Displays has Fidelity Comparable to RB69 DNA Polymerase In vitro fidelity assays were carried out on the 5' end $^{32}$P labeled primer P2 annealed to template T2 (5'-TTTTTTTTA-CACGCAAACCGCCTCTCCCCGC-3') (SEQ ID NO. 4). Each reaction mixture contained 0.5 μM RB69 DNA polymerase or F6, 3.3 nM annealed primer-template, 250 μM dTTP, 25 mM Tris-Cl pH7.5, 60 mM KCl, 10 mM DTT, 200 μg/ml BSA, and 1 mM EDTA. Reactions were initiated by the addition of MgCl₂ to a final concentration of 6 mM and stopped at different time points by the addition of loading buffer containing 83% (v/v) formamide, 0.01% (w/v) xylene cyanol, 0.01% (w/v) bromphenol blue and 33 mM EDTA. The products were analyzed by separation on a 20% polyacrylamide-7M urea gel and followed by phosphorimaging.

Figure 4:
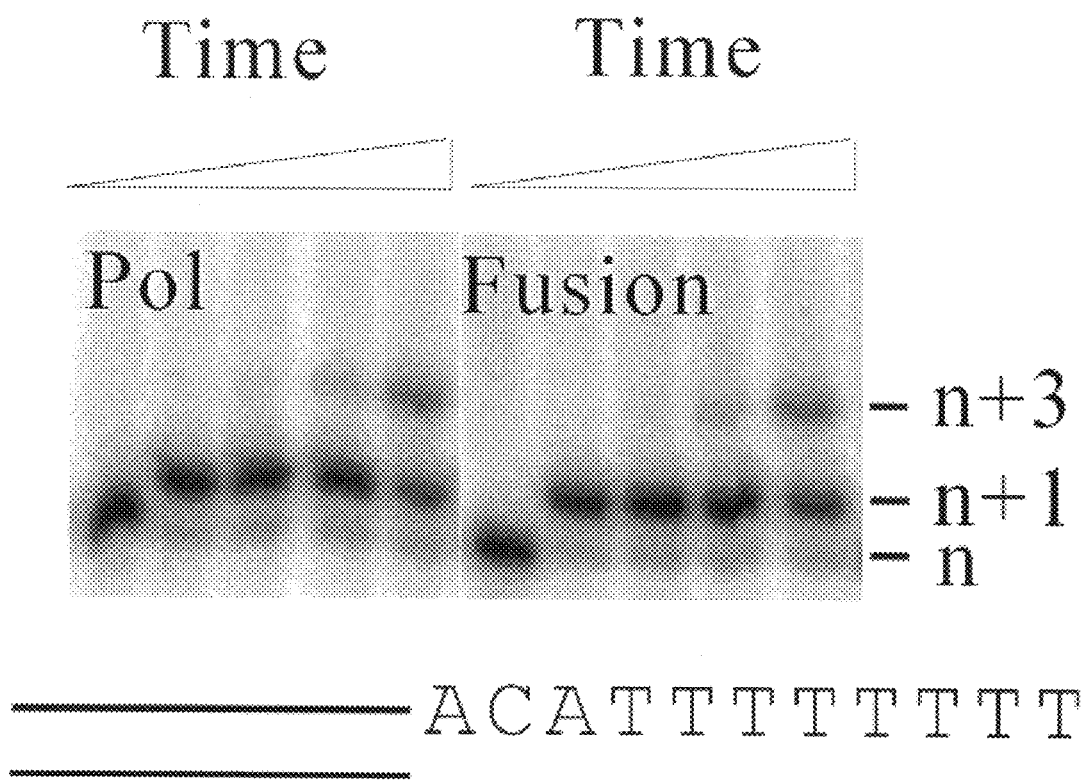
FIG. 4 is an image of the results from an in vitro fidelity assay, according to specific embodiment of the present disclosure involving the sequence ACATTTTTTT (SEQ ID NO. 5).

Fidelity is as important an attribute as processivity in DNA replication. The addition of the RB69 SSB ssDNA binding domain could have altered DNA polymerase interactions to the template strand in an unforeseen manner and resulted in altered fidelity. To investigate the fidelity of F6, dNTP misincorporation into primer-templates was measured using a template of sufficient length to allow the binding of both the polymerase and SSB. $^{32}$P labeled primer-template was incubated with an excessive amount of DNA polymerase or F6 and only dTTP (FIG. 4). The first unpaired base in the template is A and one T was rapidly added to the primer strand to give the N+1 product. The second unpaired base in the template is C. Since dTTP is highly in excess, rare mis-incorporation events can be qualitatively observed by the incorporation of dTTP at the N+2 position. Since the third unpaired base in the template is A, N+2 product was immediately extended to N+3 product. Both RB69 DNA polymerase and F6 have comparable levels of fidelity based on this qualitative result, as shown in FIG. 4.

F6 has Higher Affinity for Primer-Template Junction than RB69 DNA Polymerase.

Binding affinities of RB69 DNA polymerase and F6 to a primer-template DNA were measured by nitrocellulose filter binding assays. Concentration of annealed 5' end $^{32}$P labeled P2/T2 was set at least 10 fold below the $K_d$ and protein concentration was varied. Labeled DNA and protein were incubated in a total volume of 230 μl assay buffer containing 10 mM Tris-Cl pH 7.5, 50 mM NaCl, 0.1 mM EDTA, 5% (v/v) DMSO, 0.3 mM DTT and 0.1 mg/ml BSA for 30 mins before filtering though nitrocellulose filter paper. Protein-bound radiolabeled DNA was detected and quantified using a Fuji phosphorimager. Data (Y) were analyzed with IgorPro (Wavemetrics, CA) to estimate values for the variables in the following equation:

$$Y = Y_0 + \frac{1}{2}\Delta Y_{max}\left[\left(1+\frac{K_d+P_0}{D_0}\right) - \sqrt{\left(1+\frac{K_d+P_0}{D_0}\right)^2 - \frac{4P_0}{D_0}}\right]$$

$Y_0$ is the level of background radioactivity detected when no DNA is bound, $Y_{max}$ is the level of radioactivity measured when 100% of the DNA was in complex with protein, $K_d$ is the equilibrium dissociation constant, $P_0$ is the concentration of protein added, and $D_0$ is the concentration of DNA.

Figure 5:
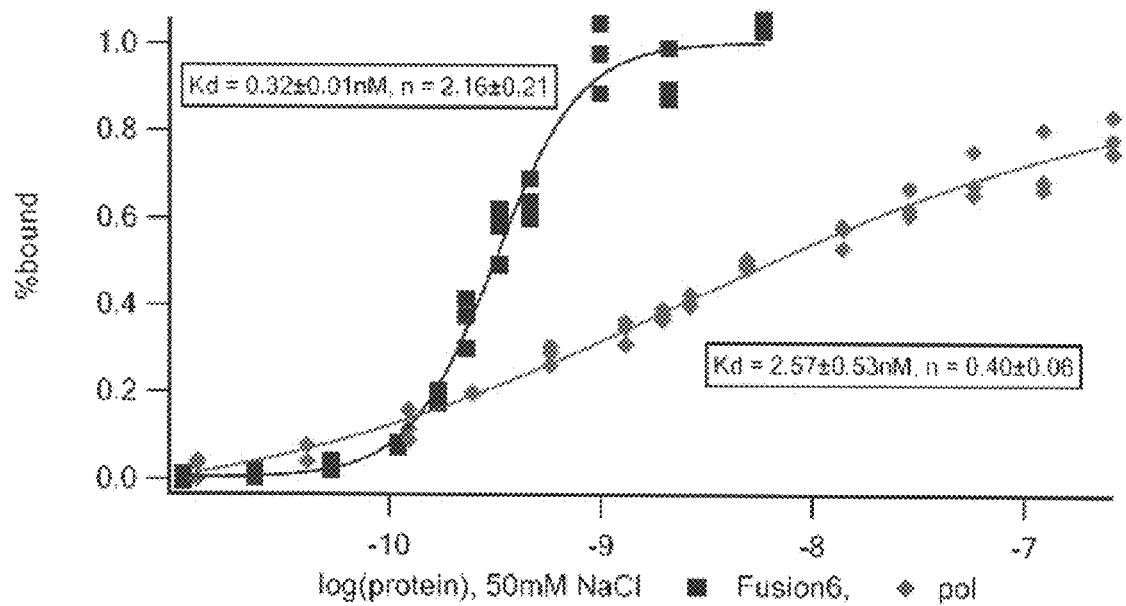
FIG. 5 is a graph of the results from a filter binding assay, according to specific example embodiments of the present disclosure.

Binding curves for RB69 DNA polymerase (red diamond) and F6 (blue square) to a primer-template junction are shown in FIG. 5. Each data point was obtained by incubating fixed concentration of 5' $^{32}$P labeled primer-template DNA with a range of concentrations of protein in a total volume of 230 µl assay buffer in a 96 well plate for 30 min. The samples were then passed through a nitrocellulose filter paper. The filter paper was exposed to a phospher imaging plate overnight and the amount of bound DNA was measured by radioactivity. The curves were fitted using the Igor software application and using three repetitions of data.

As shown in FIG. 6, F6 binds to primer-template DNA 6-fold tighter than RB69 DNA polymerase (Table 2). These results are in good agreement with earlier studies on the affinity of RB69 DNA polymerase for primer-template DNA at this pH and ionic strength as described in Sun S & Shamoo Y. *J Biol Chem* 2003; 278(6):3876-3881.

TABLE 2

| Protein | Dissociation constant (nM) |
|---|---|
| F6 | 0.38 ± 0.06 |
| RB69 DNA polymerase | 2.17 ± 0.31 |

RB69 SSB Core Crystallization and Structure Determination

RB69 SSB core domain crystals were grown by vapor diffusion in hanging drops at 20° C. 1.5 µl SSB core domain was mixed with 1.5 µl well solution containing 30% PEG200 (v/v), 50 mM MES, pH 6.0, 10 mM MgCl$_2$. Tetragonal rod shaped crystals grew within 3 days. RB69 SSB core domain crystals diffracted to 2.0 Å using home source X-ray. Data were collected on an RAXIS4++ detector and processed with Crystal Clear and d*trek 31 (Table III). There are two copies of RB69 SSB core in each asymmetric unit. The structure was solved by molecular replacement in CNS using T4 SSB core structure (1GPC) as a search model (90% identical). The structure was manually rebuilt in O, refined in CNS and deposited (PDB 2A1K).

F6 Crystallization

Native F6 crystals were grown by vapor diffusion in hanging drops at 20° C. 1.5 µl F6 was mixed with 1.5 µl well solution containing 16-18% PEG400, 0.1M Tris-Cl, pH8.0. Hexagonal rod shaped crystals grew within 2 days. Diffraction quality SeMet F6 crystals required 3% (v/v) 6-Aminocaproic acid as an additive in the growing condition.

F6 Data Collection and Processing and Structure Refinement

Native and SeMet F6 crystals were transferred to a cryo-protectant (35% PEG400, 0.1M Tris-Cl, pH8.0) by gradually increasing PEG400 concentration and were flash frozen. Both selenomethione and native crystals diffracted to 3.2 Å and data were collected at APS SBC 19ID beamline (Table 3). Crystals were cryo-cooled at 100K for data collection. Data were processed with HKL2000. The F6 structure was solved by a combination of MAD and molecular replacement. 25 out of 30 SeMet peaks were located using program SHELXD and positions refined in SHARP. Phases were calculated to 4 Å and underwent density modification in SHARP. Experimental phases were then used for phased translation in CNS using the RB69 DNA polymerase structure (1IH7). Attempts to locate the position of SSB core by phased translation in CNS and CCP4 were not successful and therefore SSB core was positioned manually into experimentally phased maps. Positioning of SSB was confirmed by anomalous peaks arising from 2 SeMet residues and electron density for the Zn$^{2+}$ of the zinc binding site of SSB that was not included in the original model. The structure was manually rebuilt in O, refined in CNS and deposited (PDB 2ATQ).

TABLE 3

| | RB69 SSB core | F6 Native | F6 λ1 | F6 λ2 |
|---|---|---|---|---|
| Data collection | | | | |
| Wavelength (Å) | 1.5418 | 0.95372 | 0.97942 | 0.97956 |
| Resolution (Å) | 2.0 | 38-3.2 | 38-3.2 | 38-3.45 |
| Space group | P4$_3$ | P6$_5$ | P6$_5$ | P6$_5$ |
| Unit Cell (Å) | a = b = 67.98 | a = b = 196.03 | a = b = 195.61 | |
| | c = 124.38 | c = 85.170 | c = 85.02 | |
| Unique reflections | 36718 | 30717 | 30873 | 24753 |
| Average redundancy | 3.7 | 5.3 | 5.1 | 5.0 |
| I/sigma$^d$ | 5.6 (1.3) | 19.5 (2.6) | 16.9 (2.3) | 17.5 (3.7) |
| Completeness (%) | 96.3 (93.1) | 99.3 (99.8) | 99.8 (99.6) | 99.8 (100) |
| R$_{merge}$ (%)$^e$ | 8.9 (34.4) | 6.8 (52.0) | 9.9 (58.9) | 9.8 (48.0) |
| Phasing power$^f$ | N/A | N/A | 3.346 | 1.817 |
| Refinement | | | | |
| Resolution (Å) | 48-2.0 | 38-3.2 | | |
| R$_{working}$ (%)$^g$ | 24.0 (31.0) | 27.5 (34.4) | | |
| R$_{free}$ (%)$^h$ | 26.3 (35.0) | 32.3 (35.9) | | |
| Average B factor for protein | 31.30 | 85.7 | | |
| Average B factor for Zinc | 25.65 | 125.21 | | |
| r.m.s.d. bonds (Å)/angles (°) | 0.008/1.2 | 0.009/1.6 | | |
| Ramachandran analysis$^i$ Disallowed | 0 | 0 | | |

Figure 7:
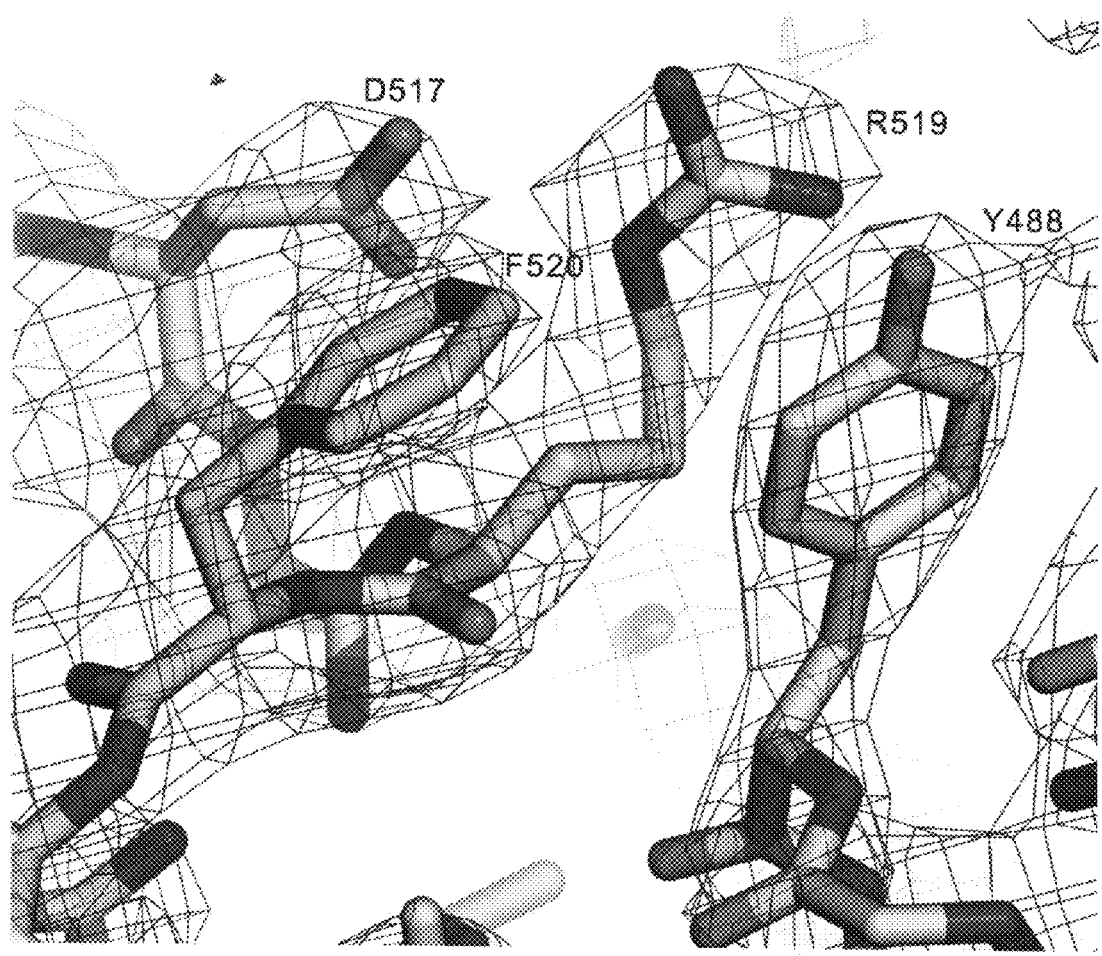
FIG. 7 is a chimeric protein structure composite omit map showing part of the density for DNA polymerase in F6 at 1.5σ level generated using PYMOL, according to specific example embodiments of the present disclosure.

$^d$Values in parentheses correspond to the last shell.
$^e$R$_{merge}$ = ΣI − <I>/ΣI, where I is measured intensity for reflections with indices hkl.
$^f$Phasing power = [|Fh(calc)|/phase-integrated lack of closure]
$^g$R$_{working}$ = Σ||F$_{obs}$| − |F$_{calc}$||/Σ|F$_{obs}$|
$^h$R$_{free}$ has the same formula as R$_{working}$ except that calculation was made with the structure factors from the test set
$^i$Calculated by using PROCHECK The structure of RB69 SSB core was solved by molecular replacement to 2.0 Å and was then used in the F6 structure determination. The structure of F6 was determined to 3.2 Å resolution using a combination of MAD and molecular replacement (FIG. 7-9). Initial attempts to solve the structure solely by molecular replacement were unsatisfactory. Although DNA polymerase could be located by molecular replacement, little electron density was observed for SSB in Fo-Fc maps. Phases determined by MAD were able to produce substantially better electron density for both RB69 SSB and DNA polymerase. Final refinement was done in a native data set. The final structure has an $R_{free}$=32.3% and $R_{working}$=27.5%. SSB has a much higher average B factor than DNA polymerase (FIG. 7-9). The linker and C-terminal 12 residues of SSB are highly flexible and were not observed in electron density maps.

Structure refinement was done in CNS and model rebuilding in O. The ribbon structure of an F6 crystal is shown in FIG. 10—SSB is in cyan and DNA polymerase in violet. The linker was designed to be highly flexible and therefore was not seen in the electron density. Black arrow pointing from the C-terminus of SSB to N-terminus of DNA polymerase indicates where the linker region should be. Diagram is generated using PYMOL.

Although SSB is near the N-terminal template entry channel of DNA polymerase, crystal packing forces could easily play an important role in positioning SSB. This is especially true given the evidence for a weak and highly flexible interaction between DNA polymerase and SSB. SSB has weaker density and much higher average B factors than DNA polymerase in the crystal structure, suggesting SSB is more mobile than the DNA polymerase. This is consistent with a replisome that allows highly flexible articulation between DNA polymerase and its cognate accessory proteins.

The above example demonstrates, among other things, that an F6 displays about a 7-fold increase in processivity compared to RB69 DNA polymerase, yielded products of much longer size, has comparable fidelity as RB69 DNA polymerase, and binds to primer-template junction about 6-fold tighter than RB69 DNA polymerase. By way of explanation, and not of limitation, tighter binding to primer-template junction and SSB's ssDNA secondary structure annealing function may be reasons for the higher processivity of F6.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A chimeric protein comprising a binding domain comprising the RB69 SSB core domain joined to a thermophilic nucleic acid polymerase domain.

2. The protein of claim 1, further comprising a double-stranded-binding domain.

3. The protein of claim 1, wherein the binding domain and the thermophilic nucleic acid polymerase domain are joined by a tether.

4. The protein of claim 1, wherein the thermophilic nucleic acid polymerase domain comprises the RB69 DNA polymerase.

5. A system comprising a nucleic acid molecule and a chimeric protein having at least two heterologous domains, wherein a first domain that is a binding domain comprising the RB69 SSB core domain is joined to a second domain that is a thermophilic nucleic acid polymerase domain; and an aqueous solution that permits the binding domain to bind to the nucleic acid molecule and that permits the chimeric protein to function in a catalytic manner to modify the nucleic acid molecule.

6. The system of claim 5, wherein the chimeric protein further comprises a third heterologous domain that comprises a double-stranded-binding domain.

7. The system of claim 5, wherein the binding domain and the thermophilic nucleic acid polymerase domain are joined by a tether.

8. The system of claim 5, wherein the thermophilic nucleic acid polymerase domain comprises the RB69 DNA polymerase.

* * * * *

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Chemically synthesized amino acid sequence

<400> SEQUENCE: 1

Gly Thr Gly Ser Gly Thr
 1               5

<210> SEQ ID NO 2
<211> LENGTH: 20
<212> TYPE: DNA
<213> ORGANISM: Artificial Sequence
<220> FEATURE:
<223> OTHER INFORMATION: Chemically synthesized DNA replication primer

<400> SEQUENCE: 2
ccagtcacga cgttgtaaaa                                                  20

<210> SEQ ID NO 3
<211> LENGTH: 20
<212> TYPE: DNA
<213> ORGANISM: Artificial Sequence
<220> FEATURE:
<223> OTHER INFORMATION: Chemically synthesized DNA replication primer

<400> SEQUENCE: 3
gcggggagag gcggtttgcg                                                  20

<210> SEQ ID NO 4
<211> LENGTH: 31
<212> TYPE: DNA
<213> ORGANISM: Artificial Sequence
<220> FEATURE:
<223> OTHER INFORMATION: Chemically synthesized DNA replication primer

<400> SEQUENCE: 4
```

```
tttttttac acgcaaaccg cctctccccg c                                31
```

<210> SEQ ID NO 5
<211> LENGTH: 11
<212> TYPE: DNA
<213> ORGANISM: Artificial Sequence
<220> FEATURE:
<223> OTHER INFORMATION: Chemically synthesized DNA replication primer

<400> SEQUENCE: 5

```
acatttttt t                                                      11
```